United States Patent [19]
Campbell et al.

[11] Patent Number: 5,672,694
[45] Date of Patent: Sep. 30, 1997

[54] β-SARCOGLYCAN NUCLEIC ACID SEQUENCE, AND NUCLEIC ACID PROBES

[75] Inventors: Kevin P. Campbell; Leland Lim; Franck Duclos; Yoshihide Sunada, all of Iowa City, Iowa; Jacques S. Beckmann, Charenton-le-Pont, France; Odile Broux, L'Hay-les-Roses, France; Fernando M. S. Tome, Paris, France; Michel Fardeau, Sceaux, France; Charles E. Jackson, Grosse Pointe, Mich.

[73] Assignee: University of Iowa Research Foundation, Iowa City, Iowa

[21] Appl. No.: 547,182

[22] Filed: Oct. 24, 1995

[51] Int. Cl.[6] .................. C07H 19/00; C07H 21/02; C07H 21/04; C12Q 1/68
[52] U.S. Cl. .................. 536/22.1; 435/6; 536/23.1; 536/23.2; 536/24.32
[58] Field of Search .................. 536/22.1, 23.1, 536/23.2, 24.31; 435/6

[56] References Cited

PUBLICATIONS

Speer et al., *Am. J. Hum. Genet.* 50: 1211 (1992).
Bashir et al. *Hum. Mol. Genet.* 3: 455 (1994).
Ben Othmane et al., *Nature Genet.* 2: 315 (1992).
Azibi et al., *Hum. Mol. Genet.* 2: 1423 (1993).
Beckmann et al., *C.R. Acad. Sci. Paris* 312: 141 (1991).
Roberds et al., *Cell* 78: 625 (1994).
Richard et al., *Cell* 81: 27 (1995).
New England Biolab Catalog, Beverly, MA, USA, p. 56 and p. 61 1986.
Sigma Chemical Company Catalog, p. 1639 1990.

*Primary Examiner*—Ardin H. Marschel
*Assistant Examiner*—Jezia Riley
*Attorney, Agent, or Firm*—Kevin M. Farrell

[57] ABSTRACT

Disclosed herein is a substantially pure nucleic acid sequence encoding a mammalian 43 kDa non-dystrophin component (β-sarcoglycan) of the dystrophin-glycoprotein complex. Also disclosed are immunogenic peptides which, when used to immunize a mammal, stimulate the production of antibodies which bind specifically to the β-sarcoglycan. Mutations in the β-sarcoglycan gene which are associated with autosomal recessive limb-girdle muscular dystrophy are also disclosed. The identification of such mutations enables the design of nucleic acid probes which hybridize specifically to a mutant form of β-sarcoglycan, or the complement thereof, but not to the DNA of the wild-type form of the gene (or the complement thereof), under stringent hybridization conditions. Such probes are useful, for example, in connection with the diagnosis of autosomal recessive limb-girdle muscular dystrophy. In addition, the identification of such mutations enables the diagnosis of autosomal recessive limb-girdle muscular dystrophy through the use of direct DNA sequencing techniques.

17 Claims, 2 Drawing Sheets

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 1225 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 10..966

( x i ) SEQUENCE DESCRIPTION: SEQ ID NO:1:

GGCACGAGG ATG GCG GCA GCG GCG GCG GCG GCT GCA GAA CAG CAA AGT     48
         Met Ala Ala Ala Ala Ala Ala Ala Ala Glu Gln Gln Ser

|     |     |     | 1   |     |     |     | 5   |     |     |     |     | 10  |     |     |     |      |
| --- | --- | --- | --- | --- | --- | --- | --- | --- | --- | --- | --- | --- | --- | --- | --- | ---- |
| TCC | AAT | GGT | CCT | GTA | AAG | AAG | TCC | ATG | CGT | GAG | AAG | GCT | GTT | GAG | AGA | 96   |
| Ser | Asn | Gly | Pro | Val | Lys | Lys | Ser | Met | Arg | Glu | Lys | Ala | Val | Glu | Arg |      |
|     |     | 15  |     |     |     | 20  |     |     |     |     | 25  |     |     |     |     |      |
| AGG | AGT | GTC | AAT | AAA | GAG | CAC | AAC | AGT | AAC | TTT | AAA | GCT | GGA | TAC | ATT | 144  |
| Arg | Ser | Val | Asn | Lys | Glu | His | Asn | Ser | Asn | Phe | Lys | Ala | Gly | Tyr | Ile |      |
|     | 30  |     |     |     |     | 35  |     |     |     |     | 40  |     |     |     | 45  |      |
| CCG | ATT | GAT | GAA | GAT | CGT | CTC | CAC | AAA | ACA | GGG | TTG | AGA | GGA | AGA | AAG | 192  |
| Pro | Ile | Asp | Glu | Asp | Arg | Leu | His | Lys | Thr | Gly | Leu | Arg | Gly | Arg | Lys |      |
|     |     |     |     | 50  |     |     |     |     | 55  |     |     |     |     | 60  |     |      |
| GGC | AAT | TTA | GCC | ATC | TGT | GTG | ATT | ATC | CTC | TTG | TTT | ATC | CTG | GCT | GTC | 240  |
| Gly | Asn | Leu | Ala | Ile | Cys | Val | Ile | Ile | Leu | Leu | Phe | Ile | Leu | Ala | Val |      |
|     |     |     | 65  |     |     |     |     | 70  |     |     |     |     | 75  |     |     |      |
| ATC | AAT | TTA | ATA | ATA | ACA | CTT | GTT | ATT | TGG | GCC | GTG | ATT | CGC | ATT | GGA | 288  |
| Ile | Asn | Leu | Ile | Ile | Thr | Leu | Val | Ile | Trp | Ala | Val | Ile | Arg | Ile | Gly |      |
|     |     | 80  |     |     |     |     | 85  |     |     |     |     | 90  |     |     |     |      |
| CCA | AAT | GGC | TGT | GAT | AGT | ATG | GAG | TTT | CAT | GAA | AGT | GGC | CTG | CTT | CGA | 336  |
| Pro | Asn | Gly | Cys | Asp | Ser | Met | Glu | Phe | His | Glu | Ser | Gly | Leu | Leu | Arg |      |
|     | 95  |     |     |     |     | 100 |     |     |     |     | 105 |     |     |     |     |      |
| TTT | AAG | CAA | GTA | TCT | GAC | ATG | GGA | GTG | ATC | CAC | CCT | CTT | TAT | AAA | AGC | 384  |
| Phe | Lys | Gln | Val | Ser | Asp | Met | Gly | Val | Ile | His | Pro | Leu | Tyr | Lys | Ser |      |
| 110 |     |     |     |     | 115 |     |     |     |     | 120 |     |     |     |     | 125 |      |
| ACA | GTA | GGA | GGA | AGG | CGA | AAT | GAA | AAT | TTG | GTC | ATC | ACT | GGC | AAC | AAC | 432  |
| Thr | Val | Gly | Gly | Arg | Arg | Asn | Glu | Asn | Leu | Val | Ile | Thr | Gly | Asn | Asn |      |
|     |     |     |     | 130 |     |     |     |     | 135 |     |     |     |     | 140 |     |      |
| CAG | CCT | ATT | GTT | TTT | CAG | CAA | GGG | ACA | ACA | AAG | CTC | AGT | GTA | GAA | AAC | 480  |
| Gln | Pro | Ile | Val | Phe | Gln | Gln | Gly | Thr | Thr | Lys | Leu | Ser | Val | Glu | Asn |      |
|     |     |     | 145 |     |     |     |     | 150 |     |     |     |     | 155 |     |     |      |
| AAC | AAA | ACT | TCT | ATT | ACA | AGT | GAC | ATC | GGC | ATG | CAG | TTT | TTT | GAC | CCG | 528  |
| Asn | Lys | Thr | Ser | Ile | Thr | Ser | Asp | Ile | Gly | Met | Gln | Phe | Phe | Asp | Pro |      |
|     |     | 160 |     |     |     |     | 165 |     |     |     |     | 170 |     |     |     |      |
| AGG | ACT | CAA | AAT | ATC | TTA | TTC | AGC | ACA | GAC | TAT | GAA | ACT | CAT | GAG | TTT | 576  |
| Arg | Thr | Gln | Asn | Ile | Leu | Phe | Ser | Thr | Asp | Tyr | Glu | Thr | His | Glu | Phe |      |
|     | 175 |     |     |     |     | 180 |     |     |     |     | 185 |     |     |     |     |      |
| CAT | TTG | CCA | AGT | GGA | GTG | AAA | AGT | TTG | AAT | GTT | CAA | AAG | GCA | TCT | ACT | 624  |
| His | Leu | Pro | Ser | Gly | Val | Lys | Ser | Leu | Asn | Val | Gln | Lys | Ala | Ser | Thr |      |
| 190 |     |     |     |     | 195 |     |     |     |     | 200 |     |     |     |     | 205 |      |
| GAA | AGG | ATT | ACC | AGC | AAT | GCT | ACC | AGT | GAT | TTA | AAT | ATA | AAA | GTT | GAT | 672  |
| Glu | Arg | Ile | Thr | Ser | Asn | Ala | Thr | Ser | Asp | Leu | Asn | Ile | Lys | Val | Asp |      |
|     |     |     |     | 210 |     |     |     |     | 215 |     |     |     |     | 220 |     |      |
| GGG | CGT | GCT | ATT | GTG | CGT | GGA | AAT | GAA | GGT | GTA | TTC | ATT | ATG | GGC | AAA | 720  |
| Gly | Arg | Ala | Ile | Val | Arg | Gly | Asn | Glu | Gly | Val | Phe | Ile | Met | Gly | Lys |      |
|     |     |     | 225 |     |     |     |     | 230 |     |     |     |     | 235 |     |     |      |
| ACC | ATT | GAA | TTT | CAC | ATG | GGT | GGT | AAT | ATG | GAG | TTA | AAG | GCG | GAA | AAC | 768  |
| Thr | Ile | Glu | Phe | His | Met | Gly | Gly | Asn | Met | Glu | Leu | Lys | Ala | Glu | Asn |      |
|     |     | 240 |     |     |     |     | 245 |     |     |     |     | 250 |     |     |     |      |
| AGT | ATC | ATC | CTA | AAT | GGA | TCT | GTG | ATG | GTC | AGC | ACC | ACC | CGC | CTA | CCC | 816  |
| Ser | Ile | Ile | Leu | Asn | Gly | Ser | Val | Met | Val | Ser | Thr | Thr | Arg | Leu | Pro |      |
|     | 255 |     |     |     |     | 260 |     |     |     |     | 265 |     |     |     |     |      |
| AGT | TCC | TCC | AGT | GGA | GAC | CAG | TTG | GGT | AGT | GGT | GAC | TGG | GTA | CGC | TAC | 864  |
| Ser | Ser | Ser | Ser | Gly | Asp | Gln | Leu | Gly | Ser | Gly | Asp | Trp | Val | Arg | Tyr |      |
| 270 |     |     |     |     | 275 |     |     |     |     | 280 |     |     |     |     | 285 |      |
| AAG | CTC | TGC | ATG | TGT | GCT | GAT | GGG | ACG | CTC | TTC | AAG | GTG | CAA | GTA | ACC | 912  |
| Lys | Leu | Cys | Met | Cys | Ala | Asp | Gly | Thr | Leu | Phe | Lys | Val | Gln | Val | Thr |      |
|     |     |     |     | 290 |     |     |     |     | 295 |     |     |     |     | 300 |     |      |
| AGC | CAG | AAC | ATG | GGC | TGC | CAA | ATC | TCA | GAC | AAC | CCC | TGT | GGA | AAC | ACT | 960  |
| Ser | Gln | Asn | Met | Gly | Cys | Gln | Ile | Ser | Asp | Asn | Pro | Cys | Gly | Asn | Thr |      |
|     |     |     | 305 |     |     |     |     | 310 |     |     |     |     | 315 |     |     |      |
| CAT | TAAAAGAACC | CCAGAGGTCA | CCAACATGTT | TATATCTTGA | CTTGACTTTT |     |     |     |     |     |     |     |     |     |     | 1013 |
| His |     |     |     |     |     |     |     |     |     |     |     |     |     |     |     |      |

```
TTATGCATGC  AAATCATTGT  TTTTACAGAG  TTTGTGATAA  CTCATAATTA  TTTTAATGGC  1073

AGAGCACTGC  TGTATCTGTT  TTATGGTCTA  CATAGTTAAA  ATCTTCTCAG  AGAGCCTAAA  1133

TTCTAATACA  TTTTATTAAT  TTATACTAAT  CTTCATATTT  ACTGTTCTCT  AAAATAATTA  1193

TGAGAAGCAA  ATAAAATCAA  AAGTCATGTT  TA                                  1225
```

( 2 ) INFORMATION FOR SEQ ID NO:2:

( i ) SEQUENCE CHARACTERISTICS:
        ( A ) LENGTH: 318 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ala  Ala  Ala  Ala  Ala  Ala  Ala  Ala  Glu  Gln  Gln  Ser  Ser  Asn  Gly
 1                    5                        10                       15

Pro  Val  Lys  Lys  Ser  Met  Arg  Glu  Lys  Ala  Val  Glu  Arg  Arg  Ser  Val
               20                        25                       30

Asn  Lys  Glu  His  Asn  Ser  Asn  Phe  Lys  Ala  Gly  Tyr  Ile  Pro  Ile  Asp
          35                        40                       45

Glu  Asp  Arg  Leu  His  Lys  Thr  Gly  Leu  Arg  Gly  Arg  Lys  Gly  Asn  Leu
     50                        55                       60

Ala  Ile  Cys  Val  Ile  Ile  Leu  Leu  Phe  Ile  Leu  Ala  Val  Ile  Asn  Leu
65                       70                       75                       80

Ile  Ile  Thr  Leu  Val  Ile  Trp  Ala  Val  Ile  Arg  Ile  Gly  Pro  Asn  Gly
               85                        90                       95

Cys  Asp  Ser  Met  Glu  Phe  His  Glu  Ser  Gly  Leu  Leu  Arg  Phe  Lys  Gln
               100                      105                      110

Val  Ser  Asp  Met  Gly  Val  Ile  His  Pro  Leu  Tyr  Lys  Ser  Thr  Val  Gly
          115                      120                      125

Gly  Arg  Arg  Asn  Glu  Asn  Leu  Val  Ile  Thr  Gly  Asn  Asn  Gln  Pro  Ile
     130                      135                      140

Val  Phe  Gln  Gln  Gly  Thr  Thr  Lys  Leu  Ser  Val  Glu  Asn  Asn  Lys  Thr
145                      150                      155                      160

Ser  Ile  Thr  Ser  Asp  Ile  Gly  Met  Gln  Phe  Phe  Asp  Pro  Arg  Thr  Gln
               165                      170                      175

Asn  Ile  Leu  Phe  Ser  Thr  Asp  Tyr  Glu  Thr  His  Glu  Phe  His  Leu  Pro
               180                      185                      190

Ser  Gly  Val  Lys  Ser  Leu  Asn  Val  Gln  Lys  Ala  Ser  Thr  Glu  Arg  Ile
          195                      200                      205

Thr  Ser  Asn  Ala  Thr  Ser  Asp  Leu  Asn  Ile  Lys  Val  Asp  Gly  Arg  Ala
     210                      215                      220

Ile  Val  Arg  Gly  Asn  Glu  Gly  Val  Phe  Ile  Met  Gly  Lys  Thr  Ile  Glu
225                      230                      235                      240

Phe  His  Met  Gly  Gly  Asn  Met  Glu  Leu  Lys  Ala  Glu  Asn  Ser  Ile  Ile
               245                      250                      255

Leu  Asn  Gly  Ser  Val  Met  Val  Ser  Thr  Thr  Arg  Leu  Pro  Ser  Ser  Ser
               260                      265                      270

Ser  Gly  Asp  Gln  Leu  Gly  Ser  Gly  Asp  Trp  Val  Arg  Tyr  Lys  Leu  Cys
          275                      280                      285

Met  Cys  Ala  Asp  Gly  Thr  Leu  Phe  Lys  Val  Gln  Val  Thr  Ser  Gln  Asn
     290                      295                      300

Met  Gly  Cys  Gln  Ile  Ser  Asp  Asn  Pro  Cys  Gly  Asn  Thr  His
305                      310                      315
```

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

```
GCCGGGATCC GTGATTCGCA TTGGACCAAA                              30
```

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:4:

```
GCGCGAATTC CTTTGTTGTC CCTTGCTGAA                              30
```

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:5:

```
TATCTTCTAA TGTCTTCTGT CTAT                                    24
```

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:6:

```
GAAACAAGAA TAACATGCCA TTT                                     23
```

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:7:

```
GTTTTCAGC AAGGGACAAG                                          20
```

( 2 ) INFORMATION FOR SEQ ID NO:8:

( i ) SEQUENCE CHARACTERISTICS:

( A ) LENGTH: 20 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:8:

GTTTTTCAGC AAGGGACAAC          20

( 2 ) INFORMATION FOR SEQ ID NO:9:

( i ) SEQUENCE CHARACTERISTICS:
( A ) LENGTH: 20 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:9:

TATTTTGAGT CCTCGGGTCA          20

( 2 ) INFORMATION FOR SEQ ID NO:10:

( i ) SEQUENCE CHARACTERISTICS:
( A ) LENGTH: 20 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:10:

CTTTTCACTC CACTTGGCAA          20

( 2 ) INFORMATION FOR SEQ ID NO:11:

( i ) SEQUENCE CHARACTERISTICS:
( A ) LENGTH: 11 amino acids
( B ) TYPE: amino acid
( D ) TOPOLOGY: linear ( i i ) MOLECULE TYPE: peptide ( x i ) SEQUENCE DESCRIPTION: SEQ ID NO:11:

Ala Gly Tyr Ile Pro Ile Asp Glu Asp Arg Leu
1               5                   10

( 2 ) INFORMATION FOR SEQ ID NO:12:

( i ) SEQUENCE CHARACTERISTICS:
( A ) LENGTH: 64 amino acids
( B ) TYPE: amino acid
( D ) TOPOLOGY: linear ( i i ) MOLECULE TYPE: peptide ( x i ) SEQUENCE DESCRIPTION: SEQ ID NO:12:

Val Ile Arg Ile Gly Pro Asn Gly Cys Asp Ser Met Glu Phe His Glu
1               5                   10                  15

Ser Gly Leu Leu Arg Phe Lys Gln Val Ser Asp Met Gly Val Ile His
                20                  25                  30

Pro Leu Tyr Lys Ser Thr Val Gly Gly Arg Arg Asn Glu Asn Leu Val
            35                  40                  45

Ile Thr Gly Asn Asn Gln Pro Ile Val Phe Gln Gln Gly Thr Thr Lys
        50                  55                  60

β-SARCOGLYCAN NUCLEIC ACID SEQUENCE, AND NUCLEIC ACID PROBES

BACKGROUND OF THE INVENTION

The dystrophin-glycoprotein complex (DGC) is a large oligomeric complex of sarcolemmal proteins and glycoproteins. It consists of dystrophin, a large, F-actin binding intracellular protein; syntrophin, a 59 kDa intracellular protein triplet; adhalin, a 50 kDa transmembrane glycoprotein; a 43 kDa transmembrane glycoprotein doublet (β-dystroglycan and A3b); a 35 kDa transmembrane glycoprotein; a 25 kDa transmembrane protein; and α-dystroglycan, a large extracellular laminin-binding glycoprotein. Together, the dystrophin-glycoprotein complex is believed to act as a structural link between the cytoskeleton and the extracellular matrix, thereby conferring stability to the sarcolemma and protecting muscle cells from contraction-induced damage and necrosis.

The DGC has been implicated in several forms of muscular dystrophy. In Duchenne muscular dystrophy (DMD), mutations in the dystrophin gene cause the complete absence of dystrophin and a dramatic reduction of its associated glycoproteins at the sarcolemma resulting in a severe dystrophic phenotype. In the milder Becker muscular dystrophy, mutations in dystrophin result in the production of a dysfunctional protein. More recently, severe childhood autosomal recessive muscular dystrophy (SCARMD2 or LGMD2D) was shown to be caused by missense mutations in the adhalin gene, which result in the reduction of adhalin at the sarcolemma. Non-Fukuyama congenital muscular dystrophy (CMD) has recently been linked close to the merosin locus on chromosome 6q which is likely to be responsible for this disease. Thus, in these muscular dystrophies, mutations in one component of the DGC cause the disruption of the complex and consequently lead to the dystrophic process.

The limb girdle muscular dystrophies (LGMDs) represent a clinically heterogeneous group of diseases which are characterized by progressive weakness of the pelvic and shoulder girdle muscles. These disorders may be inherited in an autosomal dominant or recessive fashion, the latter being more common with an estimated prevalence of $10^{-5}$. Several genes have been implicated in the etiology of these disorders. The autosomal dominant form, LGMD1A, was mapped to 5q22–q3425 (Speer et al., Am. J. Hum. Genet. 50:1211 (1992)), while four genes involved in the autosomal recessive forms were mapped to chromosomes 2p13—p16 (LGMD2B, Bashir et al., Hum. Mol. Genet. 3:455 (1994)), 13q12 (LGMD2C, Ben Othmane et al., Nature Genet. 2:315 (1992); Azibi et al., Hum. Mol. Genet. 2:1423 (1993)), 15q15.1 (LGMD2A, Beckmann et al., C. R. Acad. Sci. Paris 312, 141 (1991)) and 17q12–q21.33 (LGMD2D, Roberds et al. Cell 78: 625 (1994)). The genes responsible for LGMD2D and LGMD2A have been identified: the 50 kDa adhalin glycoprotein (Roberds et al., Cell 78:625 (1994)) and muscle-specific calpain (Richard et al. Cell 87:27 1995) ), respectively.

Cases of recessive limb-girdle muscular dystrophy among members of the old order of Amish of northern and southern Indiana were described by Jackson and Carey (Pediatrics 28: 77 (1961)) and Jackson and Strehler (Pediatrics 41:495 (1968)). Most of the families of these communities are interrelated by multiple consanguineous links and common ancestry which can be traced to the 18th and 19th century in the Canton of Bern, Switzerland. In view of the high consanguinity level and the similar clinical presentation of all Amish LGMD patients, the demonstration of genetic heterogeneity within this community was unexpected (Allamand et al., Hum. Mol. Genet. 4:459 (1995)). Though families from northern Indiana were shown to carry the same R769Q calpain mutation (Richard et al. Cell 87:27 1995)), involvement of this locus was excluded in Amish families from southern Indiana, as none of the examined patients from these cohorts carried this mutation, even in a heterozygous state. Furthermore, the role of known LGMD loci, as well as several other candidate regions involved in other neuromuscular disorders, were all excluded. These results thus implied the existence of yet another locus, LGMD2E, involved in autosomal recessive limb girdle muscular dystrophy. The identification and study of this locus could lead to the development of new diagnostic and/or therapeutic protocols.

SUMMARY OF THE INVENTION

In one aspect, the present invention relates to a substantially pure nucleic acid sequence encoding a mammalian 43 kDa non-dystrophin component (β-sarcoglycan) of the dystrophin-glycoprotein complex. The substantially pure nucleic acid sequence is characterized by the ability to hybridize to the DNA sequence of SEQ ID NO:1, or the complement thereof, under stringent hybridization conditions. The substantially pure nucleic acid molecule of the present invention can also be characterized as encoding the amino acid sequence shown in SEQ ID NO:2, or equivalents of said amino acid sequence. The invention also encompasses DNA expression constructs incorporating the substantially pure nucleic acid sequence encoding β-sarcoglycan, and cells (prokaryotic and eukaryotic) which harbor such an expression construct. Such compositions are useful, for example, in the production of highly pure immunogen for use in stimulating the production of polyclonal and monoclonal antibodies.

In another aspect, the present invention relates to immunogenic peptides (or equivalents thereof) which, when used to immunize a mammal, stimulate the production of antibodies which bind specifically to the β-sarcoglycan. Such peptides are useful, for example, in the production of highly pure immunogen for use in stimulating the production of polyclonal and monoclonal antibodies.

Another aspect of the present invention relates to nucleic acid probes which hybridize specifically to a mutant form of β-sarcoglycan, or the complement thereof, but not to the DNA of the wild-type form of the gene (or the complement thereof), under stringent hybridization conditions. Such probes are useful, for example, in connection with the diagnosis of autosomal recessive limb-girdle muscular dystrophy. In addition, the identification of such mutations enables the diagnosis of autosomal recessive limb-girdle muscular dystrophy through the use of direct DNA sequencing techniques.

DETAILED DESCRIPTION OF THE INVENTION

Figure 1:
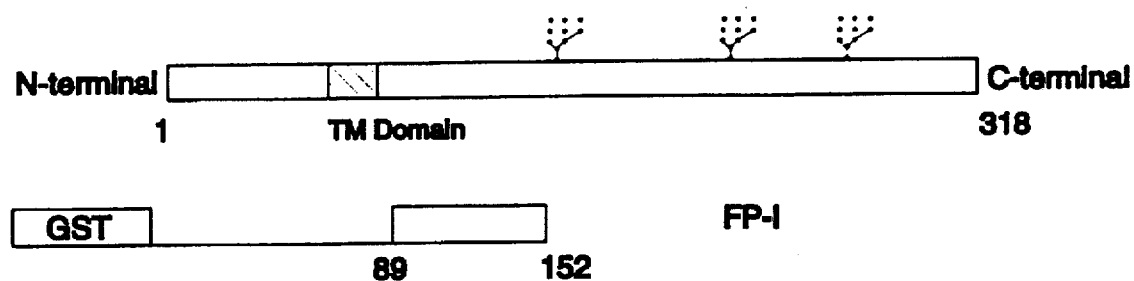
FIG. 1 is a diagrammatic representation of human β-sarcoglycan cDNA. The transmembrane domain is shaded; three sites of potential N-linked glycosylation sites are indicated.

The present invention is based, in one aspect, on the isolation of a cDNA sequence encoding a mammalian 43 kDa non-dystrophin component of the dystrophin-glycoprotein complex. This component is referred to herein as β-sarcoglycan. The isolated cDNA of the present invention can be used in a variety of contexts. For example, the sequence information disclosed herein can be used to isolate nucleic acids, other than cDNA, which encode β-sarcoglycan. Such nucleic acids include, for example, intron-containing genomic DNA sequences. Any complementary nucleic acid (both DNA and RNA) will form a duplex structure with the β-sarcoglycan sequence disclosed herein.

The isolated cDNA sequence of the present invention can be inserted in an expression vector. Such vectors contain all necessary regulatory signals to promote the expression of a DNA sequence of interest. Expression vectors are typically either prokaryote specific, or eukaryote specific. However, vectors have been developed which can promote the expression of a DNA sequence of interest in either a prokaryotic or eukaryotic system. Such vectors are known as shuttle vectors.

Prokaryotic expression vectors are useful for the preparation of large quantities (up to milligram quantities) of the protein encoded by the DNA sequence of interest. Following purification by conventional techniques, this protein, or an immunogenic portion of same, can be used, for example, as a source of highly pure immunogen for the generation of antibodies. Alternatively a crude lysate can be used in many circumstances. As disclosed in U.S. Pat. No. 5,308,752, the disclosure of which is incorporated herein by reference, levels of β-sarcoglycan are greatly reduced in an animal model for Duchenne muscular dystrophy. Thus, antibodies reactive with β-sarcoglycan, produced as described herein, are useful in connection with diagnosis of muscular dystrophy by the detection of levels.

Polyclonal antibodies can be prepared by immunizing an animal with immunogen prepared as described above using conventional techniques (see e.g., Harlow and Lane (Eds.), *Antibodies, A Laboratory Manual* (Cold Spring Harbor Laboratory, Cold Spring Harbor, N.Y. (1988)). Briefly, the immunized animal is maintained under conditions whereby antibodies reactive with the immunogen are produced. Blood is collected from the animal upon reaching a desired antibody titer. The serum containing the polyclonal antibodies is separated from the other blood components. The polyclonal antibody-containing serum can optionally be further separated into fractions of particular types of antibodies (e.g., IgG or IgM) or monospecific antibodies can be purified from polyclonal antibody containing serum.

Similarly, polyclonal antibody secreting hybridomas can be produced using conventional techniques (see e.g., Harlow and Lane (Eds.), *Antibodies, A Laboratory Manual* (Cold Spring Harbor Laboratory, Cold Spring Harbor, N.Y. (1988) )). In a preferred embodiment, anti-β-sarcoglycan monoclonal antibodies are produced by murine hybridomas formed by fusion of: a) a mouse myeloma or hybridoma which does not secrete antibody with b) murine spleen cells which secrete antibodies obtained from mice immunized against β-sarcoglycan as described in the preceding paragraph.

Typically, the mice are immunized with a primary injection of β-sarcoglycan followed by a number of boosting injections of the immunogen. During or after the immunization procedure, sera of the mice is screened to identify those mice in which a substantial immune response has been evoked. For selected mice, the spleen cells are obtained and fusions are performed. Suitable fusion techniques are the Sendai virus technique (Kohler and Milstein, *Nature* 256:495 (1975)), or the polyethylene glycol method (Kennet, "Monoclonal Antibodies, Hybridomas—A New Dimension in Biological Analysis", Eds. Kennet, McKern and Bechtol, Plenum Press, N.Y. (1980)).

The hybridomas are then screened for production of antibodies specific for β-sarcoglycan. A suitable screening technique is a solid phase radioimmunoassay. A solid phase is prepared by coupling β-sarcoglycan to an insoluble matrix. The immunoadsorbent is brought into contact with culture supernatants of hybridomas. After a period of incubation, the solid phase is separated from the supernatants, then contacted with a labeled antibody against murine immunoglobulin. Label associated with the immunoadsorbent indicates the presence of hybridoma products reactive with β-sarcoglycan.

The monoclonal antibodies can be produced in large quantities by injecting anti-β-sarcoglycan antibody producing cells into the peritoneal cavity of mice and, after an appropriate time, harvesting ascites fluid from the mice which yield a high titer of homogenous antibody. The monoclonal antibodies are then isolated from the fluid. Alternatively, the antibodies can be produced by culturing anti-β-sarcoglycan antibodies producing cells in vitro and isolating secreted monoclonal antibodies from the culture medium directly.

The Exemplification section which follows describes experiments in which two immunogenic peptides were used to immunize animals resulting in the production of antibodies which bind specifically to β-sarcoglycan. More specifically, the peptides specified in SEQ ID NOS: 11 and 12 were demonstrated to stimulate an immune response. Thus, in another aspect, the present invention relates to immunogenic peptides capable of stimulating such a response, or equivalents of such peptides. Equivalents, as used in this context, includes peptides of substantially similar length and amino acid identity to those disclosed but having a conservative amino acid substitution at a non-critical residue. A conservative amino acid substitution is a substitution in which an amino acid residue is replaced with an amino acid residue of differing identity, but whose R group can be characterized as chemically similar. Four common categories which are defined in standard biochemical texts include: polar but uncharged R groups; positively charged R groups; negatively charged R groups; and hydrophobic R groups. A preferred conservative substitution involves the substitution of a second hydrophobic residue for a first hydrophobic residue, the first and second hydrophobic residues differing primarily in the size of the R group. The hydrophobic reside would be predicted to be located internally in the folded peptide structure and the mild perturbation caused only by a change in the size of an R group at an internal location in the folded peptide structure would not be predicted to alter the antigenic properties of the peptide.

The present invention encompasses not only the nucleic acid sequence disclosed in SEQ ID NO: 1, and fragments thereof, but also related DNA sequences which hybridize to the DNA of SEQ ID NO: 1, or the complement thereof under stringent hybridization conditions. A nucleic acid sequence would fall within the scope of the invention, for example, under the following circumstances. The DNA molecule represented in SEQ ID NO: 1 is fixed to a solid support and a second DNA molecule to be tested for the ability to hybridize to the DNA of SEQ ID NO: 1 is detectably labeled and suspended in a hybridization buffer consisting essentially of 50% formamide, 5×SSPE (1×SSPE is 0.15 mM NaCl, 1 mM Na-EDTA, 10 mM Na-phosphate (pH 7.0), 5×Denhardt's solution (0.1% polyvinylpyrrolidone, 0.1% Ficoll)). The hybridization buffer is contacted with the solid support at a temperature of about 45° C. for a period of several hours. The hybridization solution is then removed, and non-specifically bound nucleic acid is removed by repeated washing with 1×SSC at increasing temperatures (up to 65° C.).

The substantially pure nucleic acid molecule of the present invention can also be characterized as encoding the amino acid sequence shown in SEQ ID NO:2, or equivalents of said amino acid sequence. Equivalents, as used in this context, includes sequences of substantially amino acid identity to those disclosed but having a conservative amino acid substitution at a non-critical residue. A conservative amino acid substitution is a substitution in which an amino acid residue is replaced with an amino acid residue of differing identity, but whose R group can be characterized as chemically similar. As discussed previously, four common categories which are defined in standard biochemical texts include: polar but uncharged R groups; positively charged R groups; negatively charged R groups; and hydrophobic R groups. A preferred conservative substitution involves the substitution of a second hydrophobic residue for a first hydrophobic residue, the first and second hydrophobic residues differing primarily in the size of the R group. The hydrophobic reside would be predicted to be located internally in the folded peptide structure and the mild perturbation caused only by a change in the size of an R group at an internal location in the folded peptide structure would not be predicted to alter the antigenic properties of the peptide.

In another aspect, the present invention relates to nucleic acid probes for the detection of a mutant form of β-sarcoglycan. This aspect of the invention is based on the discovery of specific mutations in the β-sarcoglycan gene which are associated with autosomal recessive limb-girdle muscular dystrophy. Such mutations are identified, for example, by isolating mRNA from muscle biopsy tissue from an individual to be tested (selected, for example, on the basis of clinical observations), and amplifying the β-sarcoglycan sequences by RT-PCR (see Exemplification section). Full length cDNA generated in this manner is then sequenced using standard techniques, and the sequence determined is compared to the wild-type sequence (SEQ ID NO: 1).

The three specific mutations reported in the Exemplification section which follows are a C→T change at nucleotide 350; an A→T change at nucleotide position 364; and a C→G change at nucleotide position 461. These mutations resulted in the following changes at the amino acid level: Ser→Phe; Ile→Phe; and Thr→Arg, respectively. The design of nucleic acid probes which hybridize specifically to the mutant sequences, but not to the wild-type β-sarcoglycan sequence, is a matter of routine experimentation to one of skill in the art. In preferred embodiments, such probes have a length of between about 20–30 nucleotides, with a single mismatch relative to the wild-type sequence.

Such probes can be used in a method for diagnosing autosomal recessive limb-girdle muscular dystrophy. Such diagnostic methods can be carried out, for example, to confirm a diagnosis in a symptomatic individual. In addition, such methods can be used for screening purposes in presymptomatic individuals, and prenatally.

Such diagnostic methods are performed by isolating nucleic acids from an individual and testing the diagnostic probes of the invention for the ability to hybridize to the isolated nucleic acid. In light of the fact that all of the identified mutations fall within an exon sequence, the isolated nucleic acid can be genomic DNA, cDNA or mRNA which corresponds to the disclosed target. The isolated nucleic acid can be amplified, for example, by the polymerase chain reaction prior to hybridization diagnosis. The diagnostic hybridization is carried out under stringent hybridization conditions so that the diagnostic probes do not hybridize specifically to the corresponding wild-type sequence. An example of such conditions would include the use of a hybridization buffer consisting essentially of 5×SSPE (1×SSPE is 0.15 mM NaCl, 1 mM Na-EDTA, 10 mM Na-phosphate (pH 7.0), 5×Denhardt's solution (0.1% polyvinylpyrrolidone, 0.1% Ficoll)). In a preferred embodiment, the isolated nucleic acid is fixed to a solid support (e.g., nitrocellulose filter) using standard techniques. The hybridization buffer is contacted with the isolated DNA fixed to the solid support at a temperature of about 45° C. for a period of several hours. The hybridization solution is then removed, and non-specifically bound nucleic acid is removed by repeated washing with 1×SSC at increasing temperatures (up to 65° C.).

In addition to the use of hybridization probes for the detection of autosomal recessive limb-girdle muscular dystrophy, the invention also relates to direct sequencing methods for determining such a myopathy. As discussed, the cDNA sequence of the human β-sarcoglycan gene is disclosed in SEQ ID NO: 1. By identifying flanking regions adjacent to the target regions identified in the present application, it is a routine matter to design primers which can be used to initiate DNA sequencing reactions. Such sequencing reactions can be used to determine whether the β-sarcoglycan gene of an individual contains any of the mutations disclosed herein.

One convenient approach to the direct sequencing method is to isolate mRNA from muscle biopsy. cDNA is then produced from the mRNA, and the cDNA is amplified by the polymerase chain reaction. The amplified product is then sequenced using the dideoxy chain termination method.

A second convenient approach is to isolate genomic DNA and amplify exon sequences by the polymerase chain reaction. A cDNA probe complementary to the β-sarcoglycan gene can be used to screen a genomic DNA library in order to identify genomic DNA clones which encode the β-sarcoglycan gene. In order to amplify complete exon sequences, it is necessary to define primers which will hybridize specifically to intron sequences flanking the exons. This is accomplished by first determining the location of intron sequences in selected genomic DNA clones. The most rapid method for determining this information is to use primers within each of a pair of adjoining exons to amplify the intron between them. If this is unsuccessful (e.g., when an intron is extremely long), screening of a genomic DNA library with exonic sequences can yield clones containing adjacent intron sequences. Sequencing primers are then designed which can be used to prime a sequencing reaction from the known exon sequences present in the cDNA into the unknown intron sequences. Intron sequence determined in this manner provides the sequence information necessary to design primers which are useful for amplifying the flanking exon sequences.

EXEMPLIFICATION

I. Results

β-sarcoglycan cDNA and primary structure

The dystrophin-glycoprotein complex (DGC) was identified in 1989 based on the ability of dystrophin to be retained on a wheat-germ agglutin column. When β-dystroglycan, a 43 kDa DAG, was cloned, the translated peptide sequence was compared with peptide sequence fragments obtained from the 43 kDa band of the purified DGC. Of these fragments, only one was found in the primary structure of β-dystroglycan. This suggested the presence of another protein of similar molecular weight, consistent with the observed 43 kDa doublet in the DGC (Ervasti et al., *Nature* 345:315 (1990); Yoshida, M., and Ozawa, E., *J. Biochem.* 108:748 (1990)). To further investigate this protein, the unidentified peptides were used to search the GenBank database of expressed sequence tags (dbEST) using the TBLASTN search program (Altschul et al., *J. Mol. Biol.* 21:403 (1990)). Several ESTs encoding peptide sequence fragments of the β-sarcoglycan protein were identified, all of which were isolated from a normalized human infant brain cDNA library. Two clones from which ESTs were generated, clones 22297 and 25556, were received from the IMAGE Consortium at the Lawrence Livermore National Laboratories. The larger of these two clones, 25556, was sequenced fully on both strands. In addition, clones were isolated from a λZAPII human skeletal muscle cDNA library using the 1225 bp insert of clone 25556 as a probe. Sequence analysis revealed a single open reading frame that encodes a protein with a predicted molecular weight of 34,777 Da (SEQ ID NO:1). Several peptide fragments obtained from sequencing of the 43 kDa doublet were found in the primary structure of the protein. No significant homology with any other known protein was detected by database search. In addition, evidence of alternate polyadenylation was obtained from our sequence data. Two distinct poly(A)+ tails have been identified, one that is about 300 bases downstream of the stop codon, and one that is approximately 3 kb downstream.

Hydropathy analysis of the amino acid sequence revealed a single transmembrane domain and no functional signal sequence at the N-terminus. Thus, the small N-terminal domain of the protein is predicted to be intracellular, whereas the large C-terminus is extracellular. This membrane topology is consistent with the location of the three putative N-linked glycosylation sites, all of which are C-terminal to the transmembrane domain. In addition, there is one potential intracellular consensus site for phosphorylation by protein kinase C or casein kinase II at Ser[21]. The predicted membrane organization is similar to that of β-dystroglycan and adhalin, both of which have large extracellular and short intracellular domains (Ibraghimov-Beskrovnaya et al., *Nature* 355:696 (1992); Roberds et al., *J. Biol. Chem.* 268:23739 (1993)).

Tissue distribution of β-sarcoglycan

To determine the tissue-specific expression of the β-sarcoglycan, RNA hybridization analysis was performed. Human adult and fetal multiple tissue northern blots were probed in two different ways: once with a $^{32}P$-labeled PCR fragment which encompassed bases 132–465 of the β-sarcoglycan coding region, and a second time with the 1225 bp insert of clone 25556 described above. The predominant transcript is approximately 4.4 kb in length; however, there are also weaker signals of 3.0 and 1.35 kb. Sequence data demonstrating evidence of alternate polyadenylation can account for the smallest and largest transcript. β-sarcoglycan RNA is present in all tissues, and is particularly enriched in skeletal and cardiac muscle. This pattern of expression is different from adhalin, which is expressed only in muscle tissue, but is similar to dystroglycan, which is ubiquitously expressed. Interestingly, the northern blot results are different between the two probes. When probed with the PCR fragment, the signals in the fetal liver and adult pancreas lanes are weak or absent. However, when probed with the larger clone, which contains all the coding region and nearly 300 bp of 3' untranslated region, these signals are significantly stronger, particularly in the adult pancreas. This suggests that the 5' end of the coding region is alternatively spliced among different tissues. This alternative splicing could also account for the 3.0 kb transcript.

Identification and localization of β-sarcoglycan protein in normal muscle

To confirm that the cloned cDNA represents the 43 kDa dystrophin-associated glycoprotein, a glutathione-S-transferase (GST) fusion protein (FP-I) containing 64 residues C-terminal to the transmembrane domain was constructed (FIG. 1). Anti-FP-I polyclonal antibodies were produced in rabbits, and were used to determine the presence of β-sarcoglycan in isolated membranes and purified DGC. The antibody specifically recognizes a 43 kDa protein in both crude sarcolemma and purified DGC, but does not recognize GST alone. In addition, sheep polyclonal antibodies produced against a peptide fragment (residues 42–52) of the β-sarcoglycan protein also recognized a 43 kDa protein in the purified DGC. Identification of β-sarcoglycan during the purification of the DGC demonstrates that β-sarcoglycan is an integral component of the DGC.

To determine the subcellular localization of β-sarcoglycan by immunofluorescence, serial transverse cryosections of control human biopsied skeletal muscle were immunostained with anti-FP-I antibody pre-absorbed with GST, as well as with antibodies against other components of the DGC including dystrophin, β-dystroglycan, syntrophin, adhalin and 35 kDa DAG. These experiments revealed that the anti-FP-I antibody labeled throughout the entire sarcolemma and showed colocalization of β-sarcoglycan with other components of the DGC.

Localization of the β-sarcoglycan gens to Chromosome 4q12

To determine the chromosomal location of the β-sarcoglycan gens, primers derived from the EST Z43241 were designed to amplify a fragment of the human β-sarcoglycan gene from a panel of human-rodent somatic cell hybrids containing various combinations of human chromosomes. Restriction digests of the amplified product with TaqI specifically cleaved the human allele, and allowed us to assign the β-sarcoglycan gene to chromosome 4. To further narrow the chromosomal region, the same process was used to analyze DNA isolated from human-rodent somatic cell hybrids containing various fragments of chromosome 4 (Mills et al., *Genomics* 14:209 (1992). β-sarcoglycan fragments could be amplified only from hybrids containing the region 4p14–q21.1, which overlaps the centromere.

To perform fluorescence in situ hybridization (FISH), two cosmids spanning approximately 40 kb of the human β-sarcoglycan gene were isolated by screening a human chromosome 4 cosmid library. The smaller cosmid, which contained a 28.5 kb insert, was used as a probe and resulted in the specific labeling of the centromere on the long arm of chromosome 4, corresponding to band 4q12.

A search for polymorphic microsatellites within the β-sarcoglycan gene was undertaken. Southern blots of restriction fragments of the cosmids and genomic PCR fragments were probed with oligonucleotides encoding a dinucleotide (CA) repeat and several tetranucleotide repeats. Only hybridization with the CA repeat oligonucleotide was detected. Sequencing subsequently located a novel CA repeat within an intron of the β-sarcoglycan gene between nucleotides 438 and 439 of the cDNA sequence. This sequence was found to be polymorphic, with nine alleles and has an observed heterozygosity of 67% based on the study of eight CEPH reference families.

Linkage of the β-sarcoglyoan gene in an Amish isolate from Southern Indiana

In the course of the investigation of the β-sarcoglycan protein, six previously-described southern Indiana Amish families (Allamand et al., *Hum. Mol. Genet.* 4:459 (1995)) were subjected to a systematic linkage search using the highly informative microsatellites described by Gyapay et al. (*Nature Genet.* 7:246 (1994)). Over 75% of the genome was excluded upon analysis of 320 microsatellite markers until a lod score of 1.12 was obtained at θ=0.0 with marker D4S428, indicative of potential linkage. Twenty-nine additional microsatellite markers of the pericentromeric region of chromosome 4 were subsequently genotyped; almost all of them demonstrated linkage to the disease locus in these families.

Figure 2:
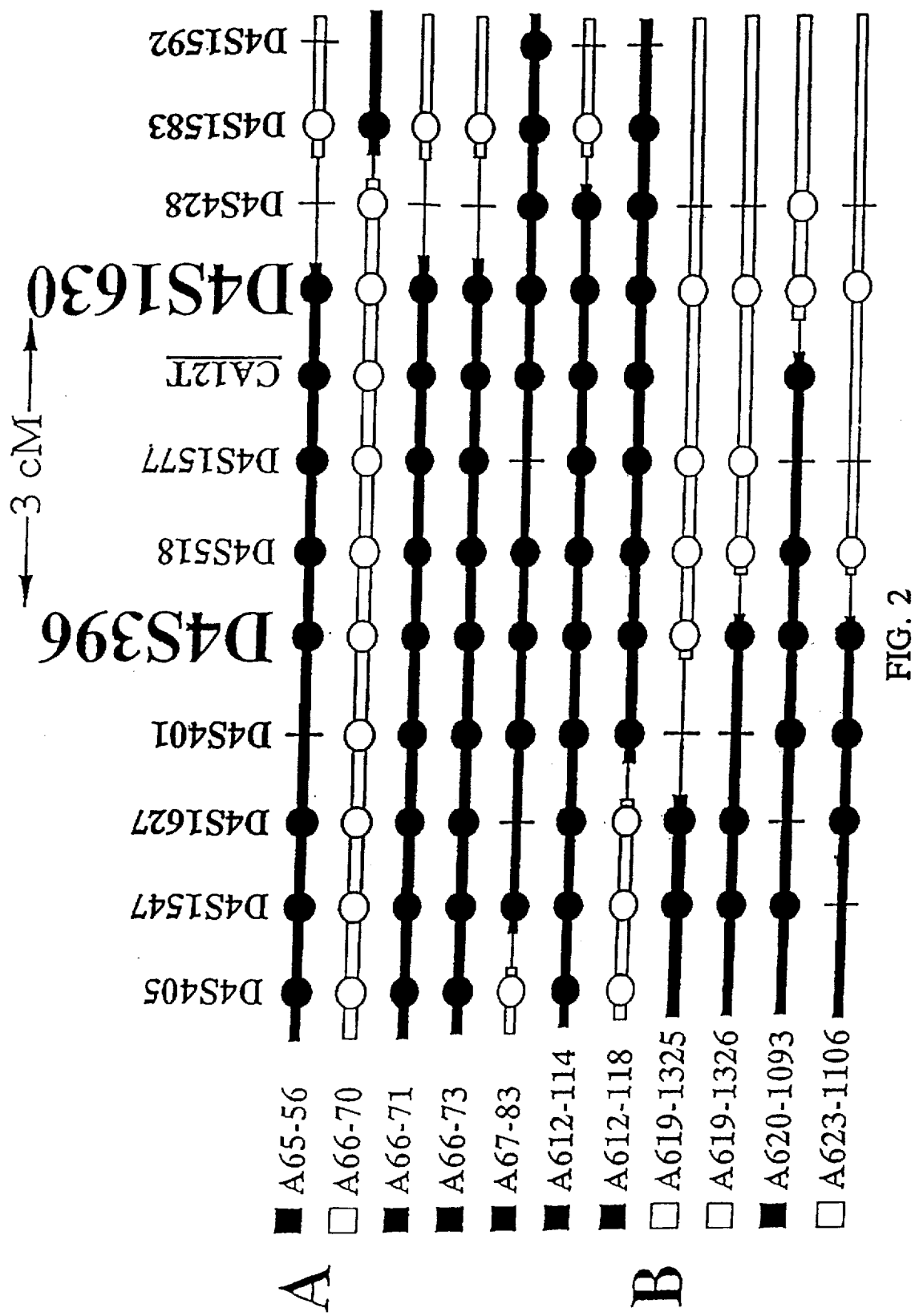
FIGS. 2A and 2B are diagrammatic representations of recombinant haplotypes in LGMD2E families. The ordered marker loci have arbitrarily been represented as equidistant. Loci bracketing the smallest interval defined by recombination events are noted in larger letters, and the intragenic β-sarcoglycan microsatellite is underlined. Solid squares indicate affected individuals whereas open squares represent healthy carriers. The numbers indicate the family and the individual. Parental alleles or chromosomes segregating with the disease allele or the normal allele are coded as solid or open circles, respectively. Thin horizontal lines represent the recombination interval. Uninformative markers are coded by a line in place of a circle, and nongenotyped markers are left blank. The last two recombinants define the critical interval for the location of the morbid locus.

In autosomal recessive disorders, affected individuals from consanguineous families often show homozygosity by descent at the region surrounding a disease locus (Lander, E. S., and Botstein, D., *Science* 236:1567 (1987)). Haplotypes were manually constructed for the chromosome 4 markers assuming a minimal number of recombinations. A unique carrier haplotype segregating within all the southern Indiana Amish population was identified, suggestive of a unique founder effect, though different from the one found in the northern Indiana and Pennsylvania Amish LGMD2A families (Allamand et al., *Hum. Mol. Genet.* 4:459 (1995)). Six affected and one nonaffected offspring showed informative crossovers (FIG. 2A). This allowed the recognition of D4S1547 and D4S1583 as new flanking loci which define a region of approximately 9 cM, based on analyses of CEPH reference families (Gyapay et al., *Nature Genet.* 7:246 (1994)).

Five additional southern Indiana LGMD families were also shown to be linked to this new locus, thereby increasing the number of informative meioses. A maximum lod score of 11.72 at θ=0.0 was obtained with marker D4S518 (Table 1). Genotyping of these families with new microsatellite markers allowed a further narrowing of the LGMD2E interval, flanked by markers D4S396 and D4S1630 (FIG. 2B). In addition, homozygosity mapping and reconstitution of historical crossing overs suggested that the LGMD2E interval is flanked by markers D4S396 and D4S428.

Based on physical maps for chromosome 4 (Cohen et al., *Nature* 366:698 (1993)), CEPH YACs spanning this region were used to localize the β-sarcoglycan gene inside the LGMD2E interval, between markers D4S1577 and D4S1630. Genotyping of the intragenic microsatellite in LGMD2E families yielded a lod score of 7.26 at θ=0.0 (Table 1). The lower lod score value, as compared to D4S518, is due to the reduced informativity of this marker in these families.

Identification of a mutation in Amish LGMD2E patients

To characterize β-sarcoglycan in these families, Northern blot analysis was performed on total RNA isolated from skeletal muscle biopsies of two affected siblings to determine whether β-sarcoglycan mRNA size or abundance were affected. The major muscle β-sarcoglycan transcript (4.4 kb) was present at normal levels and size in both affected sibs compared to an unrelated control. This strongly suggested that the causative mutation was most likely to involve a small deletion, insertion, or base substitution.

To address this question, fragments of the β-sarcoglycan cDNA were amplified following reverse-transcription from total RNA prepared from biceps brachii muscle biopsies of these two affected sibs. The RT-PCR products were sequenced, and a single transversion from C to G at nucleotide 461 was detected in both patients in a homozygous state. The codon change is ACA to AGA and results in a Thr→Arg substitution at residue 151 (T151R).

Segregation of this mutation was assessed in this family and in other Amish LGMD2E families by sequencing and "touchdown" PCR (Don et al., *Nucleic Acids Res.* 19:4008 (1991)). Results showed perfect cosegregation of this missense mutation with the disease in all southern Indiana Amish families tested, as expected from the common haplotype at this locus. To exclude the possibility that this missense mutation might be a polymorphism, 122 unrelated chromosomes taken from the CEPH reference families were tested; none showed this mutation, nor did any northern Indiana LGMD2A Amish patients.

In addition to the Thr→Arg substitution at residue 151, two other mutations have been identified using the experimental procedures outlined above. More specifically, a C→T change at nucleotide 350 results in a Ser→Phe change at codon position 114, and an A→T change at nucleotide position 364 results in an Ile→Phe change at codon 119.

Demonstration of β-sarcoglycan deficiency in LGMD2E muscle

To test the effects of the T151R mutation on β-sarcoglycan expression in Amish LGMD2E patients, the skeletal muscle biopsy specimens from the two patients described above were examined by immunofluorescence. Serial frozen sections were stained with antibodies against β-sarcoglycan (anti-FP-I) or other DGC components as described above. Dystrophin, β-dystroglycan, syntrophin and laminin α2 chain were present at comparable levels with control muscle. However, the immunostaining of β-sarcoglycan was greatly decreased, with a concomitant reduction of adhalin and the 35 kDa DAG.

II. Experimental Procedures

Peptide sequencing and isolation of expressed sequence tags

The 43 kDa band of the purified dystrophin-glycoprotein complex (Ervasti et al., *Nature* 345:315 (1990)) was partially sequenced at the Howard Hughes Medical Institute Biopolymer Facility. Several peptide fragments were obtained. Peptide sequences were used to search the GenBank database of expressed sequence tags (dbEST) using the TBLASTN search program (Altschul et al., *J. Mol. Biol.* 21:403 (1990)). Several overlapping ESTs were identified that represented portions of the β-sarcoglycan cDNA.

Isolatation and characterization of human β-sarcoglycan cDNA clones and Northern blot analysis Two of the clones from which ESTs were generated, clones 22297 and 25556, were obtained from the IMAGE Consortium at Lawrence Livermore National Laboratories. The larger of the two clones, clone 25556, was fully sequenced on both strands using an Applied Biosystems, Inc. automated sequencer. This clone was determined to contain the full coding region of the β-sarcoglycan cDNA as well as the entire 3' untranslated region and a poly(A)+ tail. In addition, clones were isolated from a λZAPII human skeletal muscle cDNA library (Stratagene) using the 1225 bp insert of IMAGE clone 25556 as a probe. Primary structure and site detection analyses were performed using PC/Gene software (Intelligenetics). CLONTECH adult and fetal human multiple tissue northern blots containing 2 μg of poly(A)+ RNA per lane were probed with a 333 bp PCR-amplified probe that represents nucleotides 132 to 465 of the β-sarcoglycan sequence. These blots were probed a second time using the 1225 bp insert clone 25556.

Fusion protein construct

A 192 bp region of the A3b cDNA downstream of the predicted transmembrane domain was amplified by PCR using the following primers: sense 5'-GCCGGGATCCGTGATTCGCATTGGACCAAA-3' (SEQ ID NO:3); antisense 5'-GCGCGAATTCCTTTGTTGTCCCTTGCTGAA-3' (SEQ ID NO:4). This PCR product was subcloned into pGEX2TK4 and introduced into E. Coli DH5α cells. 50 mL overnight cultures were diluted 1:10 and induced with IPTG to promote fusion protein (FP-I) production. Fusion proteins were purified on a glutathione-agarose column (Smith, D. B., and Johnson, K. S., "In Current Protocols in Molecular Biology", (eds. Ausubel et al.) 16.71 (Current Protocols, Brooklyn, N.Y., 1987)).

Antibodies

Anti-β-sarcoglycan antibodies were generated by intramuscular and subcutaneous injection of New Zealand white rabbits with 100 μg of purified FP-I in an emulsion of Freund's complete adjuvant. Rabbits were boosted two weeks later with a subcutaneous injection of 500 μg of FP-I in PBS (50 mM sodium phosphate, pH 7.4, 0.9% NaCl). Rabbits were bled two weeks following boost and the serum was tested for the presence of anti-FP-I antibodies. The serum was cleared of anti-GST antibodies with a glutathione column and anti-FP-I antibodies were affinity-purified using Immobilon-P strips containing 250 μg of FP-I. Monoclonal antibodies VIA4$_2$ against dystrophin, and IVD3$_1$ against adhalin were previously characterized (Ervasti et al., Nature 345:315 (1990); Jorgensen et al., J. Cell Biol. 110: 1173 (1990)). Monoclonal antibody 8D5 specifically binds β-dystroglycan. An affinity-purified rabbit antibody against 35 kDa DAG was also used in this study. Monoclonal antibody against human laminin α2 chain was purchased from Chemicon.

Western blot and immunofluorescence

KCl-washed microsomes, crude rabbit skeletal muscle sarcolemma and purified DGC were prepared as previously described (Ervasti et al., Cell 66:1121 (1991); Ohlendieck et al., J. Cell Biol. 112:135 (1991)). Proteins were resolved on a 3%–12% SDS polyacrylamide gel (Laemmli, U.K., Nature 227:680 (1970)) and transferred to nitrocellulose by electroblotting (Towbin et al., Proc. Natl. Acad. Sci. USA 76:4350 (1979)). Blots were incubated overnight in a 1:20 dilution of affinity-purified anti-FP-I antibody in Blotto (5% nonfat dried milk in TBS [20 mM Tris-HCl, 200 mM NaCl, pH 7.4]). Blots were then incubated with a horseradish peroxidase-conjugated goat anti-rabbit IgG secondary antibody (Boehringer Mannheim) for 1 hr. Antibody staining was detected with $H_2O_2$ in TBS with 4-chloro-1-naphthol as a substrate. For immunofluorescence, 7 μm transverse cryosections were prepared from control and Amish LGMD muscle. The following procedures were performed at room temperature. Sections were treated with AB blocking solutions (Vector), blocked with 5% BSA in PBS for 30 min., and then incubated with a 1:20 dilution of affinity-purified anti-FP-I antibody for 90 min. Antibodies against the following components of the DGC were also tested: dystrophin, laminin α2 chain, β-dystroglycan, syntrophin, adhalin and 35 kDa DAG. After extensive washing with PBS, sections were incubated with biotinylated secondary antibodies (1:500) for 30 min., washed with PBS, and then incubated with FITC-conjugated streptavidin (1:1000) for 30 min. After rinse with PBS, sections were mounted with FITC-guard (Testog) and observed under a Zeiss Axioplan fluorescence microscope. Photographs were taken under identical conditions with the same exposure time.

Isolation of Human β-sarcoglycan Genomic Clones and Localization of the β-sarcoglycan Gene to Chromosome 4q12

Primers corresponding to human β-sarcoglycan cDNA nucleotides 291–312 (sense) and 413–429 (anti-sense) were used in PCR using DNA from a panel of 25 human-rodent somatic cell hybrids (BIOS Corporation) containing various combinations of human chromosomes. Subsequent restriction digest of the PCR reaction by TaqI was necessary to distinguish between the human and rodent alleles. A somatic cell hybrid panel containing various regions of chromosome 4 (Mills et al., Genomics 14:209 (1992)) was used to further narrow the location of the gene using the same approach described above.

A chromosome 4 cosmid library was screened with a $^{32}$P-PCR labeled cDNA representing nucleotides 135–429. Two cosmids with inserts of 28.5 kb and 35 kb were obtained. CsCl-purified DNA from the smaller cosmid was used for fluorescence in situ hybridization mapping which was carried out by Genome Systems.

Families

Six previously described LGMD Amish families from southern Indiana (52 individuals, 13 affected) (Allamand et al., Hum. Mol. Genet. 4:459 (1995)) were analyzed in the linkage search. Subsequently, DNA from 5 additional southern Indiana families were included in this study (39 individuals, 13 affected). All of these kindreds show multiple consanguineous links.

Genotyping and Linkage Analysis

Markers were selected from the microsatellite panel described by Gyapay et al. (Nature Genet. 7:246 (1994)) or from CHLC maps (Murray et al., Science 265:2049 (1994)). Fifty ng of each DNA was used as templates in a 50 μl polymerase chain reaction as described in Fougerousse et al. (Hum. Mol. Genet. 3:285 (1994)). Southern blots of restriction fragments of cosmids were probed with CA and tetranucleotide oligonucleotide repeats labeled with γ-$^{32}$ P ATP. Subsequent subcloning and sequencing of the positive fragment was performed. The identified intragenic polymorphic CA repeat was amplified using the following primers: sense (5'-TATCTTCTAATGTCTTCTGTCTAT-3') (SEQ ID NO:5) and antisense (5'-GAAACAAGAATAACATGCCATTT-3') (SEQ ID NO:6). PCR conditions for this marker were denaturation at 94° C. for 1 min., annealing at 60° C. for 1 min. and extension at 72° C. for 1 min., for 30 cycles. Primer sequences, PCR conditions and other information concerning the highly polymorphic microsatellites used in this study can be obtained from the Genome Database, John Hopkins University. Two-point and multipoint linkage analyses were carried out using the LINKAGE software package, version 5.1 (Lathrop et al., Am. J. Hum. Genet. 37:482 (1985)), assuming fully penetrant autosomal recessive inheritance with a gene frequency of 0.001.

RNA isolation and Reverse-Transcription PCR

Total RNA was extracted from 20–30 mg of skeletal muscle from one control and two Amish LGMD2E patients from family A623 (Allamand et al., *Hum. Mol. Genet.* 4:459 (1995)) using RNAzol (Tel-Test) according to manufacturer specifications. RNA samples were run on 15% formaldehyde/1.5% agarose gels and transferred to Hybond N membrane (Amersham). Membranes were then hybridized with the PCR labeled cDNA as described above.

Approximately 1 μg of total RNA was used for reverse transcription with AMV reverse transcriptase and a specific primer representing nucleotides 1113–1132 (antisense) in the β-sarcoglycan cDNA untranslated region, in the reaction mixture (6 mM MgCl$_2$, 200 mM dNTP, 50 mM KCl, 10 mM Tris pH 8.2, 40 units RNAsin, 10 pmol specific primer) and incubated for 90 min. at 42° C. PCR on the reverse-transcribed product was performed using the same 3' primer and one of two 5' primers (representing nucleotides 1–18 and 47–68 respectively) to cover the entire β-sarcoglycan cDNA coding sequence. The RT-PCR amplification products were analyzed by agarose gel electrophoresis and by direct sequencing.

Touchdown PCR 50 ng of DNA were subjected to "Touchdown" PCR procedure (Don et al., *Nucleic Acids Res.* 19:4008 (1991)) in a 50 μl reaction mix containing 10 mM Tris-HCl, pH 8.8, 50 mM KCl, 1.5 mM MgCl2, 0.1% Triton X-100, 200 mM of each dNTP, 100 ng of each primer and 2 units of Taq Polymerase (Perkin Elmer). After 5 min. denaturation at 96° C., amplification cycles were carried out as follows: 40 sec. denaturation at 94° C. followed by 30 sec. annealing steps starting at 63° C. with a decrease of 1° C. every two cycles until 59° C. Twenty-five additional cycles of amplification consisting of 40 sec. at 94° C. and 30 sec. at 58° C. were performed. Primer pairs A461/m1 and T461/m3 were designed to yield, respectively, a 100 bp product from individuals carrying the mutation, and a 158 bp PCR product from individuals not carrying the mutation. Primers sequences were: A461: 5'-GTTTTTCAGCAAGGGACAAG-3' (SEQ ID NO:7); T461: 5'-GTTTTTCAGCAAGGGACAAC-3' (SEQ ID NO:8); m1: 5'-TATTTTGAGTCCTCGGGTCA-3' (SEQ ID NO:9); m3: 5'-CTTTTCACTCCACTTGGCAA-3' (SEQ ID NO:10). PCR products were analyzed by electrophoresis on 4% agarose gels stained with ethidium bromide.

TABLE 1

| | Markers | Z at Recombination (θ) of | | | | Zmax (θ) | One lod support interval |
|---|---|---|---|---|---|---|---|
| A | D4S1547 | —∞ | 8.00 | 8.33 | 7.57 | 5.42 | 8.43(0.032) | 0.004–0.102 |
| | D4S1627 | —∞ | 1.83 | 2.79 | 2.81 | 2.15 | 2.86(0.075) | — |
| | D4S401 | —∞ | 5.42 | 5.43 | 4.86 | 3.39 | 5.56(0.025) | 0.001–0.120 |
| | D4S396 | —∞ | 9.39 | 9.53 | 8.53 | 5.96 | 9.72(0.027) | 0.004–0.092 |
| | D4S1536 | 3.58 | 3.53 | 3.30 | 2.98 | 2.21 | 3.58(0.000) | 0.000–0.154 |
| | D4S518 | 11.72 | 11.44 | 10.28 | 8.82 | 5.92 | 11.72(0.000) | 0.000–0.035 |
| | D4S1577 | 5.08 | 4.97 | 4.51 | 3.91 | 2.65 | 5.08(0.000) | 0.000–0.086 |
| | D4S1630 | —∞ | 4.56 | 5.20 | 4.84 | 3.51 | 5.81(0.025) | 0.001–0.120 |
| | D4S428 | —∞ | 0.87 | 1.35 | 1.37 | 1.04 | 1.39(0.075) | — |
| | D4S1619 | 0.77 | .76 | .69 | .60 | 0.41 | 0.77(0.000) | — |
| | D4S2379 | —∞ | 1.83 | 2.79 | 2.81 | 2.15 | 2.86(0.075) | — |
| | D4S1583 | —∞ | −0.04 | 2.12 | 2.53 | 2.12 | 2.53(0.000) | — |
| B | CA12T | 7.26 | 7.06 | 6.27 | 5.29 | 3.41 | 7.26(0.000) | 0.000–0.050 |

Table 1. Pairwise lod scores obtained in ten southern Indiana families between the LGMD2E locus and chromosome 4 markers (A) and the intragenic microsatellite (B)
Maximum lod scores and their corresponding recombination fractions with one-lod support intervals.
Marker loci are listed according to their order on the regional map of chromosome 4.

We claim:

1. A substantially pure nucleic acid sequence encoding a mammalian 43 kDa non-dystrophin component of the dystrophin-glycoprotein complex which is characterized by the ability to hybridize to the DNA sequence of SEQ ID NO:1, or the fully complementary sequence thereof, under stringent hybridization conditions.

2. A substantially pure nucleic acid sequence of claim 1 which is of human origin.

3. A DNA expression construct comprising, in expressible form, a substantially pure deoxyribonucleic acid sequence encoding a mammalian 43 kDa non-dystrophin component of the dystrophin-glycoprotein complex which is characterized by the ability to hybridize to the DNA sequence of SEQ ID NO:1, or the fully complementary sequence thereof, under stringent hybridization conditions.

4. A DNA expression construct of claim 3 wherein the substantially pure nucleic acid is of human origin.

5. A prokaryotic cell transformed with a DNA expression construct comprising, in expressible form, a substantially pure deoxyribonucleic acid sequence encoding a mammalian 43 kDa non-dystrophin component of the dystrophin-glycoprotein complex which is characterized by the ability to hybridize to the DNA sequence of SEQ ID NO:1, or the fully complementary sequence thereof, under stringent hybridization conditions.

6. A prokaryotic cell of claim 5 wherein the substantially pure deoxyribonucleic acid sequence is of human origin.

7. A eukaryotic cell transformed with a DNA expression construct comprising, in expressible form, a substantially pure deoxyribonucleic acid sequence encoding a mammalian 43 kDa non-dystrophin component of the dystrophin-glycoprotein complex which is characterized by the ability to hybridize to the DNA sequence of SEQ ID NO:1, or the fully complementary sequence thereof, under stringent hybridization conditions.

8. A eukaryotic cell of claim 7 wherein the substantially pure deoxyribonucleic acid sequence is of human origin.

9. A substantially pure nucleic acid molecule, or the fully complementary sequence complement thereof, the substantially pure nucleic acid molecule encoding the amino acid sequence shown in SEQ ID NO:2.

10. A substantially pure nucleic acid molecule of claim 9 which is of human origin.

11. A DNA expression construct comprising, in expressible form, a substantially pure nucleic acid molecule encoding the amino acid sequence shown in SEQ ID NO:2.

12. A DNA expression construct of claim 11 wherein the substantially pure nucleic acid molecule is of human origin.

13. A prokaryotic cell transformed with a DNA expression construct comprising, in expressible form, a substantially pure nucleic acid molecule encoding the amino acid sequence shown in SEQ ID NO:2.

14. A eukaryotic cell transformed with a DNA expression construct comprising, in expressible form, a substantially pure nucleic acid molecule encoding the amino acid sequence shown in SEQ ID NO:2.

15. A nucleic acid probe of at least 20 nucleotides which hybridizes specifically to a mutant form of β-sarcoglycan, or the fully complementary sequence thereof, but not to the DNA of SEQ ID NO:1 or the fully complementary sequence thereof, under stringent hybridization conditions, the mutant form differing from the wild-type form of β-sarcoglycan in a change from threonine to arginine at codon 151 shown in SEQ ID NO:1.

16. A nucleic acid probe of at least 20 nucleotides which hybridizes specifically to a mutant form of β-sarcoglycan, or the fully complementary sequence thereof, but not to the DNA of SEQ ID NO:1 or the fully complementary sequence thereof, under stringent hybridization conditions, the mutant form differing from the wild-type form of β-sarcoglycan in a change from serine to phenylalanine at codon 114 shown in SEQ ID NO:1.

17. A nucleic acid probe of at least 20 nucleotides which hybridizes specifically to a mutant form of β-sarcoglycan, or the fully complementary sequence thereof, but not to the DNA of SEQ ID NO:1 or the fully complementary sequence thereof, under stringent hybridization conditions, the mutant form differing from the wild-type form of β-sarcoglycan in a change from isoleucine to phenylalanine at codon 119 shown in SEQ ID NO:1.

* * * * *

UNITED STATES PATENT AND TRADEMARK OFFICE
CERTIFICATE OF CORRECTION

PATENT NO.   : 5,672,694
DATED        : September 30, 1997
INVENTOR(S)  : Campbell et al.

It is certified that error appears in the above-indentified patent and that said Letters Patent is hereby corrected as shown below:

In Claim 9, line 2, delete the word "complement."

Signed and Sealed this

Third Day of February, 1998

Attest:

BRUCE LEHMAN

*Attesting Officer*   *Commissioner of Patents and Trademarks*